(12) United States Patent
Huber et al.

(10) Patent No.: US 9,561,047 B2
(45) Date of Patent: Feb. 7, 2017

(54) SURGICAL HAND GRIP AND A SURGICAL TUBULAR SHAFT INSTRUMENT WITH A SURGICAL HAND GRIP

(71) Applicant: Aesculap AG, Tuttlingen (DE)

(72) Inventors: Christian Huber, Muehlheim (DE); Pedro Morales, Tuttlingen-Nendingen (DE)

(73) Assignee: Aesculap AG, Tuttlingen (DE)

( * ) Notice: Subject to any disclaimer, the term of this patent is extended or adjusted under 35 U.S.C. 154(b) by 197 days.

(21) Appl. No.: 14/287,314

(22) Filed: May 27, 2014

(65) Prior Publication Data

US 2014/0350597 A1 Nov. 27, 2014

Related U.S. Application Data

(63) Continuation of application No. PCT/EP2012/072865, filed on Nov. 16, 2012.

(30) Foreign Application Priority Data

Dec. 2, 2011 (DE) .......................... 10 2011 056 003

(51) Int. Cl.
*A61B 17/00* (2006.01)
*A61B 17/29* (2006.01)
(Continued)

(52) U.S. Cl.
CPC .............. *A61B 17/2909* (2013.01); *B25G 3/00* (2013.01); *A61B 18/1445* (2013.01);
(Continued)

(58) Field of Classification Search
CPC ............... A61B 2017/2912; A61B 2017/2913; A61B 2017/2915; A61B 2017/2916; A61B 2017/2919; A61B 2017/292; A61B 2017/2922; A61B 17/2909
See application file for complete search history.

(56) References Cited

U.S. PATENT DOCUMENTS

| 5,735,873 A | 4/1998 | MacLean |
| 5,810,879 A | 9/1998 | de Guillebon |

(Continued)

FOREIGN PATENT DOCUMENTS

| DE | 94 09 979 | 11/1994 |
| DE | 44 21 585 | 7/1995 |

(Continued)

OTHER PUBLICATIONS

English Translation of DE 44 21 585 C1 by Google Patent website accessed on Jan. 30, 2016.*

*Primary Examiner* — Tuan V Nguyen
(74) *Attorney, Agent, or Firm* — Lipsitz & McAllister, LLC (57) ABSTRACT

A surgical hand grip for a surgical tubular shaft instrument is provided. The hand grip includes a coupling device for coupling to a tubular shaft tool having a tubular shaft and a force transmission element movable back and forth relative thereto. The coupling device has a coupling element for coupling to the force transmission element and a connecting element for connecting to the tubular shaft. A gripping device is connected to the coupling element and is transferable from a non-actuating disposition into at least one actuating disposition and vice versa thereby changing the mutual relative spacing between the coupling element and the connecting element. The hand grip has a guiding device with a guiding body for guiding the coupling element during the transfer from the non-actuating position into the at least one actuating position along a grip axis independently of the disposition of the gripping device during the transfer.

22 Claims, 5 Drawing Sheets

(51) Int. Cl.
  *B25G 3/00* (2006.01)
  *A61B 18/14* (2006.01)
  *A61B 17/30* (2006.01)
(52) U.S. Cl.
  CPC . *A61B 2017/0046* (2013.01); *A61B 2017/292* (2013.01); *A61B 2017/2946* (2013.01); *A61B 2017/305* (2013.01); *Y10T 16/469* (2015.01)

(56) References Cited

U.S. PATENT DOCUMENTS

| | | | |
|---|---|---|---|
| 5,951,574 A * | 9/1999 | Stefanchik | A61B 17/1285 227/901 |
| 6,004,320 A | 12/1999 | Casscells et al. | |
| 6,334,861 B1 | 1/2002 | Chandler et al. | |
| 8,100,907 B2 | 1/2012 | Aue | |
| 8,876,805 B2 | 11/2014 | Kaercher et al. | |
| 2002/0026202 A1 * | 2/2002 | Honey | A61B 17/221 606/127 |
| 2007/0225754 A1 * | 9/2007 | Measamer | A61B 17/2909 606/205 |
| 2008/0046003 A1 | 2/2008 | Renger et al. | |
| 2008/0064929 A1 | 3/2008 | Wiedenbein | |
| 2008/0140090 A1 * | 6/2008 | Aranyi | A61B 17/105 606/143 |
| 2008/0275441 A1 | 11/2008 | Aue | |
| 2008/0294192 A1 | 11/2008 | Stefan et al. | |
| 2011/0245864 A1 | 10/2011 | Besse et al. | |
| 2013/0172859 A1 * | 7/2013 | Kaercher | A61B 17/00234 606/1 |
| 2014/0135757 A1 | 5/2014 | Bernard et al. | |
| 2014/0142566 A1 | 5/2014 | Bernard et al. | |
| 2014/0142568 A1 | 5/2014 | Bernard et al. | |
| 2014/0155890 A1 | 6/2014 | Bernard et al. | |

FOREIGN PATENT DOCUMENTS

| | | | |
|---|---|---|---|
| DE | 10 2004 025 041 | | 12/2005 |
| DE | 69829480 | | 2/2006 |
| DE | 102006007828 | | 8/2007 |
| DE | 102006052407 | | 5/2008 |
| DE | 1020122000739 | * | 4/2012 |
| WO | 95/20921 | | 8/1995 |
| WO | WO 2009/046490 | | 4/2009 |
| WO | 2013/000465 | | 1/2013 |

* cited by examiner

SURGICAL HAND GRIP AND A SURGICAL TUBULAR SHAFT INSTRUMENT WITH A SURGICAL HAND GRIP

CROSS-REFERENCE TO RELATED APPLICATIONS

This application is a continuation of international application number PCT/EP2012/072865, filed on Nov. 16, 2012, and claims the benefit of German application number 10 2011 056 003.3, filed on Dec. 2, 2011, which are incorporated herein by reference in their entirety and for all purposes.

FIELD OF THE INVENTION

The present invention relates to a surgical hand grip for a surgical tubular shaft instrument, wherein the hand grip comprises a coupling device for coupling to a tubular shaft tool which has a tubular shaft and a force transmission element that is movable back and forth relative thereto, wherein the coupling device has a coupling element for coupling to the force transmission element and a connecting element for connecting to the tubular shaft, wherein the hand grip also comprises a gripping device which is operatively connected to the coupling element and is transferable from a non-actuating disposition into at least one actuating disposition and vice versa thereby changing the relative spacing between the coupling element and the connecting element due to the transferal of the coupling element from a non-actuating position into at least one actuating position.

Moreover, the invention relates to a surgical tubular shaft instrument having a surgical hand grip and also at least one tubular shaft tool which cooperates with the hand grip.

BACKGROUND OF THE INVENTION

A hand grip of the type specified hereinabove can be connected to a tubular shaft tool or be connectable thereto in releasable manner for the purposes of forming a tubular shaft instrument such as a surgical gripping or cutting instrument for example. The hand grip and the tubular shaft tool are coupled to one another by means of the coupling device, wherein the tubular shaft cooperates with at least one connecting element of the coupling device and wherein a plurality of connecting elements may also be provided. The force transmission element, which is usually a pulling and/or a pushing element in the form of a bar or a resilient core, is moveable back and forth within the tubular shaft. This enables relative movement of the tubular shaft and the force transmission element in the proximal-distal direction. This relative movement can be converted at the working end of the tubular shaft opposite the hand grip as required into a relative movement of jaw-parts for gripping body tissue or surgical instruments such as a needle, or into a movement of a surgical parting element for cutting through body tissue.

Herein, "proximal" and "distal" are to be understood as being with reference to the user who is manipulating the hand grip and the tubular shaft instrument. The user acts on the hand grip at the proximal end, and the tubular shaft tool extends away from the hand grip in the distal direction, wherein the working end of the tubular shaft tool is usually arranged at the distal end thereof.

For the purposes of acting on the force transmission element, the coupling device comprises the coupling element which, with the help of the gripping device, is moveable relative to the connecting element connected to the tubular shaft so that the relative movement of the force transmission element and the tubular shaft can also be obtained thereby. An effect can be produced on the coupling element by the gripping device which is transferred from the non-actuating into at least one actuating disposition so that the coupling element is thereby transferred from a non-actuating into at least one actuating position.

An object underlying the present invention is to provide a hand grip of the type specified hereinabove with which an effect upon a tubular shaft tool that is connected or connectable to the hand grip can be produced in a more user-friendly manner.

SUMMARY OF THE INVENTION

In a first aspect of the invention, a surgical hand grip for a surgical tubular shaft instrument hand grip comprises a coupling device for coupling to a tubular shaft tool which has a tubular shaft and a force transmission element that is movable back and forth relative thereto, wherein the coupling device has a coupling element for coupling to the force transmission element and a connecting element for connecting to the tubular shaft, wherein the hand grip also comprises a gripping device which is operatively connected to the coupling element and is transferable from a non-actuating disposition into at least one actuating disposition and vice versa thereby changing the relative spacing between the coupling element and the connecting element due to the transferal of the coupling element from a non-actuating position into at least one actuating position. The hand grip defines a grip axis and comprises a guiding device which has a guiding body for guiding the coupling element along the grip axis during the transfer from the non-actuating position into the at least one actuating position independently of the disposition of the gripping device during the transfer from the non-actuating disposition into the at least one actuating disposition.

In a second aspect of the invention, a surgical tubular shaft instrument comprises a hand grip of this type. The surgical tubular shaft instrument also comprises at least one tubular shaft tool which cooperates with the hand grip.

BRIEF DESCRIPTION OF THE DRAWINGS

The foregoing summary and the following description may be better understood in conjunction with the drawing figures, of which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical hand grip for a surgical tubular shaft instrument, wherein the hand grip comprises a coupling device for coupling to a tubular shaft tool which has a tubular shaft and a force transmission element that is movable back and forth relative thereto, wherein the coupling device has a coupling element for coupling to the force transmission element and a connecting element for connecting to the tubular shaft, wherein the hand grip also comprises a gripping device which is operatively connected to the coupling element and is transferable from a non-actuating disposition into at least one actuating disposition and vice versa thereby changing the relative spacing between the coupling element and the connecting element due to the transferal of the coupling element from a non-actuating position into at least one actuating position. The hand grip defines a grip axis and comprises a guiding device which has a guiding body for guiding the coupling element along the grip axis during the transfer from the non-actuating position into the at least one actuating position independently of the disposition of the gripping device during the transfer from the non-actuating disposition into the at least one actuating disposition.

During the transfer from the non-actuating position into the at least one actuating position and preferably also in the opposite direction, a defined direction of movement can be provided for the coupling element by means of the guiding body of the guiding device. The direction of movement takes place along the grip axis which is typically aligned in the proximal-distal direction and in particular, defines a proximal-distal axis. The tubular shaft tool can be constructed at least at the proximal end thereof in such a way that it defines a tool axis along which the force transmission element is moveable back and forth relative to the tubular shaft. If the tool axis can be arranged to coincide with the grip axis or can be aligned coaxially relative thereto, it then becomes possible to guide the force transmission element along the tool axis and in particular along the grip axis. The hand grip in accordance with the invention thus permits the coupling element and a force transmission element cooperating therewith to be axially guided. This then provides the possibility of bringing about a purely axial movement of the force transmission element by means of the coupling element during actuation of the gripping device independently of the disposition thereof without transverse forces being effective on the force transmission element. On the one hand, due to the prevention of transverse forces on the force transmission element, the actuating force applicable by the user on the gripping device is reduced. At the same time, the actuating force can be introduced into the tubular shaft tool to better effect by means of the hand grip, which makes for more delicate operation. As a result, for a user, the hand grip in accordance with the invention and thus a tubular shaft tool utilising it is manipulable in a simpler manner. On the other hand, the wear on the force transmission element can be reduced due to the prevention of transverse forces and the life span of a tubular shaft tool cooperating with the hand grip can thereby be increased.

It is expedient if the coupling element is guided along by the guiding body along the entire extent of the movement of the coupling element and the guiding body relative to each other. Consequently, the coupling element, and hence too the force transmission element, can be provided with a clearly defined direction of movement relative to the guiding body for the entire extent of the movement.

Provision may be made for the guiding body to provide the effective connection of the coupling element to the gripping device and to connect the coupling element and the gripping device together for this purpose.

It is preferred that the guiding body define the grip axis, and that the coupling element be guided in displaceable manner during the transfer from the non-actuating position into the at least one actuating position by the guiding body. This enables the guidance of the coupling element to be ensured in a constructionally simple and reliable manner.

Preferably, the guiding body is in the form of an axial sleeve in which the coupling element is mounted in displaceable manner. This permits of a constructionally simple and at the same time compact design of the hand grip. The sleeve is e.g. cylindrical at least in sections thereof. It may be open at a distal end thereof for the introduction of the tubular shaft and the force transmission element. Expediently, the coupling element is accommodated in the interior of the sleeve with positive engagement and is thereby mounted in displaceable manner along an axis of the sleeve which defines the grip axis.

It is of advantage if the sleeve has an axial slit-like through opening along at least a section of a displacement path which is traversed by the coupling element relative to the sleeve during the transfer from the non-actuating position into the at least one actuating position and in the opposite direction. An operative element of the hand grip by means of which the coupling element is operatively connected to the gripping device can penetrate through the slit-like through opening. An actuating force applied by the user can then be transmitted from the exterior through the sleeve to the coupling element. This makes it possible for the hand grip to be of compact design. Furthermore, provision may be made for the operative element to penetrate the through opening with positive engagement or with substantially positive engagement. This permits the operative element to be guided parallel to the grip axis by means of the sleeve and thereby allows the movement of the coupling element to be defined yet more clearly. Provision may be made for more than just one slit-like through opening and/or one operative element. For example, the gripping device comprises two gripping elements each of which is operatively connected to the coupling element by an operative element. Each of the operative elements can engage through one of the through openings.

Preferably, the sleeve has a window-like through opening which extends over a larger angular range in the circumferential direction of the grip axis than the slit-like through opening. As is detailed below, the window-like through opening for example, permits the coupling element to be disengaged relative to the guiding body either transversely or at an angle with respect to the grip axis and thereby partially engage in the through opening or pass through it. Such provision may be made, in particular, when it is intended that the coupling element should be coupled to the force transmission element or decoupled therefrom. It has been shown in practice that this thereby contributes to a compact design for the sleeve and the hand grip. Expediently, the window-like through opening is arranged to be significantly shorter than the slit-like through opening in the axial direction.

In one implementation of the hand grip in accordance with the invention, it proves in practice to be advantageous for achieving a constructionally simple design and a compact structure, if the window-like through opening is arranged on the distal side of the slit-like through opening.

The sleeve and thus the hand grip can be manufactured in a simpler way if the slit-like through opening and the window-like through opening are arranged on the same side of the sleeve in the circumferential direction of the grip axis.

For the same reason, it is of advantage if the slit-like through opening and the window-like through opening merge into one another.

In general, it is of advantage if the hand grip comprises a resilient restoring element, against the effect of which the coupling element is transferable from the non-actuating position into the at least one actuating position. This facilitates the handling of the hand grip for a user.

In particular, provision may be made for the hand grip to comprise a resilient restoring element which is arranged in the sleeve and against the effect of which the coupling element is displaceable from the non-actuating position into the at least one actuating position. The arrangement of the restoring element in the sleeve makes it possible for the hand grip to be of compact construction.

For the purposes of achieving the same advantage, the restoring element is preferably arranged on the proximal side of the coupling element and is supported at the proximal end on a supporting element which is comprised by the sleeve or is fixed thereto. On the distal side thereof, the restoring element may be supported on the coupling element. The restoring element can thus be arranged axially between the coupling element that is arranged on the distal side and the supporting element that is arranged on the proximal side, this thereby lending a compact structure to the hand grip. The supporting element can, for example, be a proximal side wall of the sleeve or a closure element which is connected to the sleeve and closes the sleeve at the proximal end thereof.

It is expedient if the gripping device comprises a first gripping element which is mounted on the guiding body or on a mounting body that is connected to the guiding body such as to be pivotal about a pivotal axis that is oriented transversely relative to the grip axis. The pivotal mounting of the first gripping element permits its clearly defined and user-friendly movement relative to the guiding body or the mounting body. For the purposes of achieving a compact structure for the hand grip, the first gripping element is expediently pivotally mounted directly on the guiding body. In the present context, "transversely relative to the grip axis" means in a plane which is oriented perpendicularly to the grip axis.

In an implementation of the hand grip, it proves to be advantageous in practice for the handling thereof, if the first gripping element is pivotally mounted at a proximal end thereof and is pivotal at a distal end relative to the guiding body. The first gripping element can thus be gripped and operated by the user in a simpler manner.

Preferably, the first gripping element is pivotally mounted at a proximal end or near a proximal end of the hand grip because this then permits the hand grip to be of compact construction.

It is preferred that, starting from a spread disposition relative to the guiding body which it adopts in the non-actuating disposition, the first gripping element is transferable into a proximity disposition relative to the guiding body which it adopts in the at least one actuating disposition, and vice versa. For the purposes of operating the hand grip, the gripping element can be transferred from the spread disposition into the proximity disposition by a pivotal movement relative to the guiding body. This facilitates the manipulation of the hand grip by a user.

It is expedient if the first gripping element is fixable in at least one actuating disposition because this then gives rise to the possibility of also fixing the coupling element and thus the force transmission element in one disposition. This, for example, is expedient if jaw-parts for gripping body tissue or a surgical instrument such as a needle for instance are arranged at the working end of the tubular shaft tool.

In the actuating disposition for example, the first gripping element is latchable to the guiding body or the mounting body. This lends itself to the hand grip having a constructionally simple design. In addition, provision may be made for the first gripping element in the latched disposition to have an abutment disposition relative to the guiding body or mounting body in which it abuts the guiding body or the mounting body and adopts a clearly defined position relative thereto.

As mentioned hereinabove, the coupling element is operatively connected to the gripping device. In a constructionally simple and reliably working implementation of the hand grip, it proves in practice to be advantageous for the hand grip to comprise a linking element which is connected to the first gripping element at a first articulated joint such that it is pivotal about a first joint axis that is oriented transversely relative to the grip axis and is connected to the coupling element at a second articulated joint such that it is pivotal about a second joint axis that is oriented transversely relative to the grip axis. In this way, the linking element can form an articulated lever in order to transfer an actuating force applied by the user from the first gripping element to the coupling element. In particular, the linking element can form the previously mentioned operative element that can engage through a slit-like through opening in the guiding body which is in the form of a sleeve.

Preferably, the second joint axis extends in a plane incorporating the grip axis. The second articulated joint can thus be moved along or in parallel with the grip axis when the gripping device is operated, which in practice proves to be advantageous for the functioning of the hand grip.

Advantageously, the first articulated joint and/or the second articulated joint are arranged on the distal side of the pivotal axis, particularly when the proximal end of the first gripping element is pivotally mounted on the guiding body or the mounting body.

For the purposes of achieving a compact structure for the hand grip, particularly in combination with the last mentioned advantageous embodiment, the second articulated joint is arranged at the proximal side of the first articulated joint when transferring the first gripping element from the non-actuating disposition into the at least one actuating disposition and vice versa.

The gripping device preferably comprises a second gripping element in order to make it easier for the user to manipulate the hand grip. Provision may preferably be made for the second gripping element to be immovably fixed to the guiding body or to the mounting body because this then lends itself to the hand grip having a simpler constructional design.

The second gripping element can also be moveable and, for example, be mounted on the guiding body or on the mounting body such as to be pivotal about a pivotal axis that is oriented transversely relative to the grip axis. Furthermore, the second gripping element may be operatively connected to the coupling element by an operative element or linking element in order to transmit an actuating force to the coupling element.

In one implementation of the hand grip, it proves in practice to be expedient for the first gripping element and/or the second gripping element to be shell-like and to at least sectionally surround the guiding body, particularly in sleeve-like manner, in the circumferential direction of the grip axis. The gripping elements are arranged on two mutually opposite sides of the grip axis for example and can be gripped and operated by the user with his palm in a simpler manner.

Furthermore, it proves to be advantageous for the first gripping element and the second gripping element to be in the form of axially extending semi-cylindrical or substantially semi-cylindrical shells between which the guiding body is accommodated.

It is of advantage if the coupling element comprises a moving member which is guided by the guiding body in moveable and in particular displaceable manner, and also a receptacle member which is coupled to the moving member and comprises a receptacle for the force transmission element. Hereby, provision may be made for the receptacle member with the receptacle for the force transmission element to be guided by the guiding body, at least in sections, along the grip axis. The movement and especially the displacement member can be connected to the receptacle member and/or be connected to the guiding body in one-piece manner.

Furthermore, it is expedient if the coupling element is transferable from a coupling disposition into an uncoupling disposition and vice versa, wherein an entry opening of the receptacle for the force transmission element is axially blocked in the coupling disposition and the entry opening is axially freed in the uncoupling disposition. This facilitates the connection of the force transmission element to the coupling element and/or the disconnection thereof, for which reason the uncoupling disposition can also be referred to as the coupling-on disposition. To this end, the coupling element can be transferred into the uncoupling disposition so that the receptacle for the force transmission element can be axially released. If the coupling element adopts the coupling disposition, the entry opening is axially blocked so that the force transmission element cannot be connected to the coupling element and/or released therefrom.

It is preferred that the receptacle member be arranged on the distal side of the moving member because this then lends itself to the hand grip having a constructionally simpler design.

In a constructionally simple design of the hand grip, the receptacle comprises a blind hole which is formed in the receptacle member incorporating a side wall slit in the axial direction and which is oriented transversely relative to the grip axis. A receptacle of this type is particularly suitable for accommodating a joint ball which is arranged in the force transmission element. The joint ball can be introduced through the entry opening into the blind hole. A bar or a core, to which the joint ball is fixed, can engage through the slit side wall of the receptacle and can be led out of the receptacle.

For the purposes of manipulating the hand grip, it proves to be expedient for the moving member and the receptacle member to be moveable relative to each other in order to transfer the coupling element from the coupling disposition into the uncoupling disposition and vice versa.

In particular, it is of advantage if the receptacle member and the moving member are pivotal relative to each other about a disengaging axis that is oriented transversely relative to the grip axis. For example, the possibility is thereby given of pivoting the receptacle member alone relative to the moving member which can maintain a stationary disposition relative to the guiding body.

For reliable functioning of the hand grip, it proves to be advantageous in practice for the disengaging axis and the grip axis to define a plane.

It is expedient if the receptacle member is pivotal away from the grip axis or towards the grip axis for the purposes of transferring the coupling element from the coupling disposition into the uncoupling disposition and vice versa. If the receptacle member is pivoted away from the grip axis, the receptacle can thereby be pivoted towards the grip axis in such a way that it is axially freed and the coupling element adopts the uncoupling disposition. If the receptacle member is pivoted towards the grip axis, the entry opening can be pivoted away from the grip axis and thus spaced therefrom whereby the receptacle can be axially blocked in such a way that the coupling element adopts the coupling disposition.

When pivoting the receptacle member relative to the grip axis, it is expedient if the guiding body in the form of a sleeve comprises the previously mentioned window-like through opening in which the receptacle member can engage or through which it can pass. As previously mentioned, a compact design can thereby be given to the hand grip.

For simplifying the handling of the hand grip, it is of advantage if the coupling element is moveable and in particular displaceable along the grip axis for the transferal from the coupling disposition into the uncoupling disposition.

Preferably the coupling element is moveable and in particular displaceable in a direction opposed to the direction of movement and in particular the direction of displacement of the coupling element from the non-actuating position into the at least one actuating position for the purposes of the transferal from the coupling disposition into the uncoupling disposition. This can thereby prevent the coupling element from being transferred unintentionally into the uncoupling disposition when the hand grip is actuated.

In a corresponding manner, it is advantageous if the gripping device is transferable in a direction opposed to that for the transferal of the gripping device from the non-actuating disposition into the at least one actuating disposition for the purposes of transferring the coupling element from the coupling disposition into the uncoupling disposition.

When transferring the coupling element from the coupling into the uncoupling disposition and/or during the transferal of the gripping device, it is preferred that the previously mentioned resilient restoring element play a supporting role.

Preferably, the guiding device comprises guidance members for guiding the coupling element during the transfer from the uncoupling disposition into the coupling disposition and/or vice versa. The coupling element can thus be transferred in a defined manner from the coupling into the uncoupling disposition and/or vice versa whereby the handling of the hand grip can be facilitated.

It is of advantage if the guiding body comprises or forms at least one guidance member or if at least one guidance member is arranged thereon, which said member cooperates with at least one guidance member that is comprised or formed by the coupling element. The provision of a guidance member on the guiding body lends itself to a constructionally simple and compact structure of the hand grip. The guidance member cooperating with the guidance member is preferably arranged on the receptacle member, which, expediently, is pivotal relative to the moving member about the disengaging axis.

In one implementation of the hand grip, it proves in practice to be expedient for one guidance member to be in the form of a guide pin which is oriented transversely relative to the grip axis and for the guidance member which cooperates therewith to be in the form of a guidance surface that is inclined to the grip axis and/or for the cooperating guidance members to be in the form of guidance surfaces which slide upon one another and are inclined to the grip axis. For example, one guide pin can cooperate with one guidance surface for guiding the coupling element from the coupling disposition into the uncoupling disposition and two guidance surfaces which slide upon one another can cooperate for the transferal from the uncoupling disposition into the coupling disposition. The guide pin can be arranged on the guiding body or be comprised or formed thereby or it can be arranged on the receptacle member. In a corresponding manner, the guidance surfaces can be guidance surfaces of the guiding body or of the receptacle member.

Furthermore, it proves to be advantageous for the purposes of producing a defined transferal of the coupling element from the coupling disposition into the uncoupling disposition, if the guiding device comprises stop members for limiting the path of movement and in particular the displacement path of the coupling element along the grip axis during the transferal from the coupling disposition into the uncoupling disposition.

In one implementation of the hand grip, it proves to be expedient for achieving a constructionally simple and compact structure, if the guiding body comprises or forms at least one stop member or if one such member which cooperates with at least one stop member that is comprised by or formed by the coupling element is arranged on the guiding body.

For example, one stop member may be in the form of a stop pin that is oriented transversely relative to the grip axis, the stop member cooperating therewith being in the form of a shoulder that is oriented transversely relative to the grip axis and arranged on the coupling element or the guiding body. The stop pin may be arranged on the guiding body or on the coupling element and in correspondence therewith, the shoulder on the coupling element or on the guiding body. For example, the shoulder is arranged on the moving member.

In one constructionally simple arrangement, in particular in the case of a guiding body in the form of a sleeve, it is expedient if the coupling element is substantially cylindrical or is cylindrical at least in sections thereof and is oriented such as to be coaxial with the grip axis.

Furthermore, provision may be made for the coupling element to be slit axially at least in sections thereof. For example, the previously mentioned linking element with which the coupling element can be coupled to the gripping device can engage in the axial slit.

As previously mentioned, the present invention also relates to a surgical tubular shaft instrument. A surgical tubular shaft instrument in accordance with the invention comprises one of the previously described hand grips and also at least one tubular shaft tool which cooperates with the hand grip. Consequently, the advantages that have already been described in conjunction with the hand grip in accordance with the invention and also the advantageous embodiments thereof can likewise be obtained so that, in respect thereof, reference should be made to the preceding explanations.

At least in the region of the proximal end thereof, the at least one tubular shaft tool can define a tool axis which is an axis of the force transmission element and the tubular shaft of the tubular shaft tool. The tool axis can be made to coincide with the grip axis or be coaxially aligned therewith.

In the case of the tubular shaft tools, these may be tubular shaft tools of various types such as those with jaw parts at the working end or those with a surgical parting device each of which can also be provided in different sizes and/or configurations in each case.

Particularly in the case of there being more than just one tubular shaft tool, it is expedient if the at least one tubular shaft tool is connectable to the hand grip in releasable manner.

Figure 1:
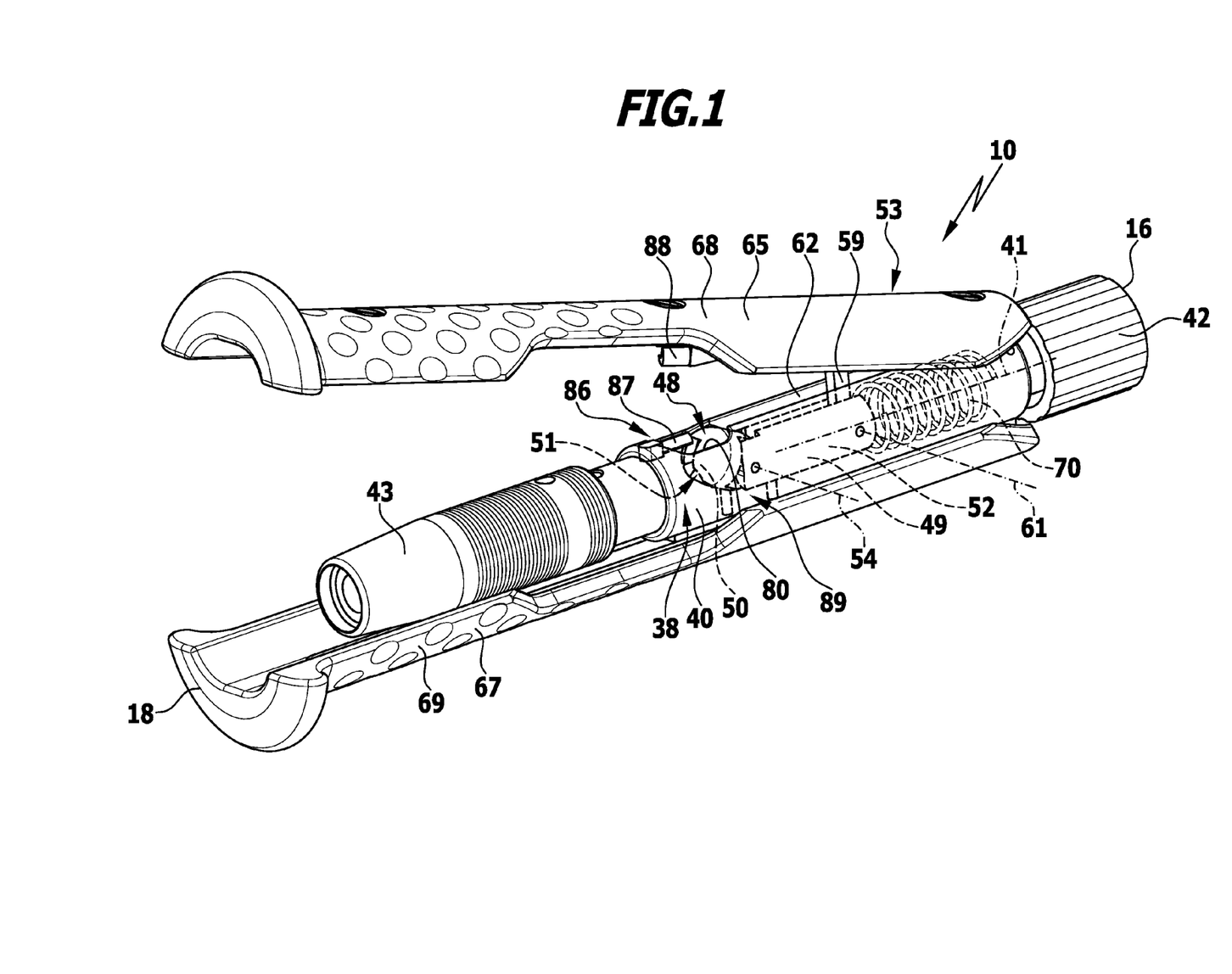
FIG. 1: shows a perspective view of a surgical hand grip in accordance with the invention.

FIG. 1 shows a preferred embodiment in the form of a perspective illustration of a surgical hand grip bearing the general reference symbol 10. The hand grip 10 can cooperate with a tubular shaft tool 12 that is partly illustrated in FIG. 2 in order provide a preferred embodiment of a surgical tubular shaft instrument in accordance with the invention bearing the general reference symbol 14. The hand grip 10 is characterized by its constructionally simple, compact and user-friendly structure which is described in the following.

The hand grip 10 has a slim, substantially longitudinally extending structure having a proximal end 16 and a distal end 18, wherein "proximal" and "distal" are to be understood as referring to a person utilising the hand grip 10. The user grips the hand grip 10 at the proximal end and acts in the distal direction on a patient who is not illustrated in the drawing. The proximal-distal direction represents the working direction along which the tubular shaft tool 12 extends when the tubular shaft instrument 14 is being used for its intended purpose.

Figure 2:
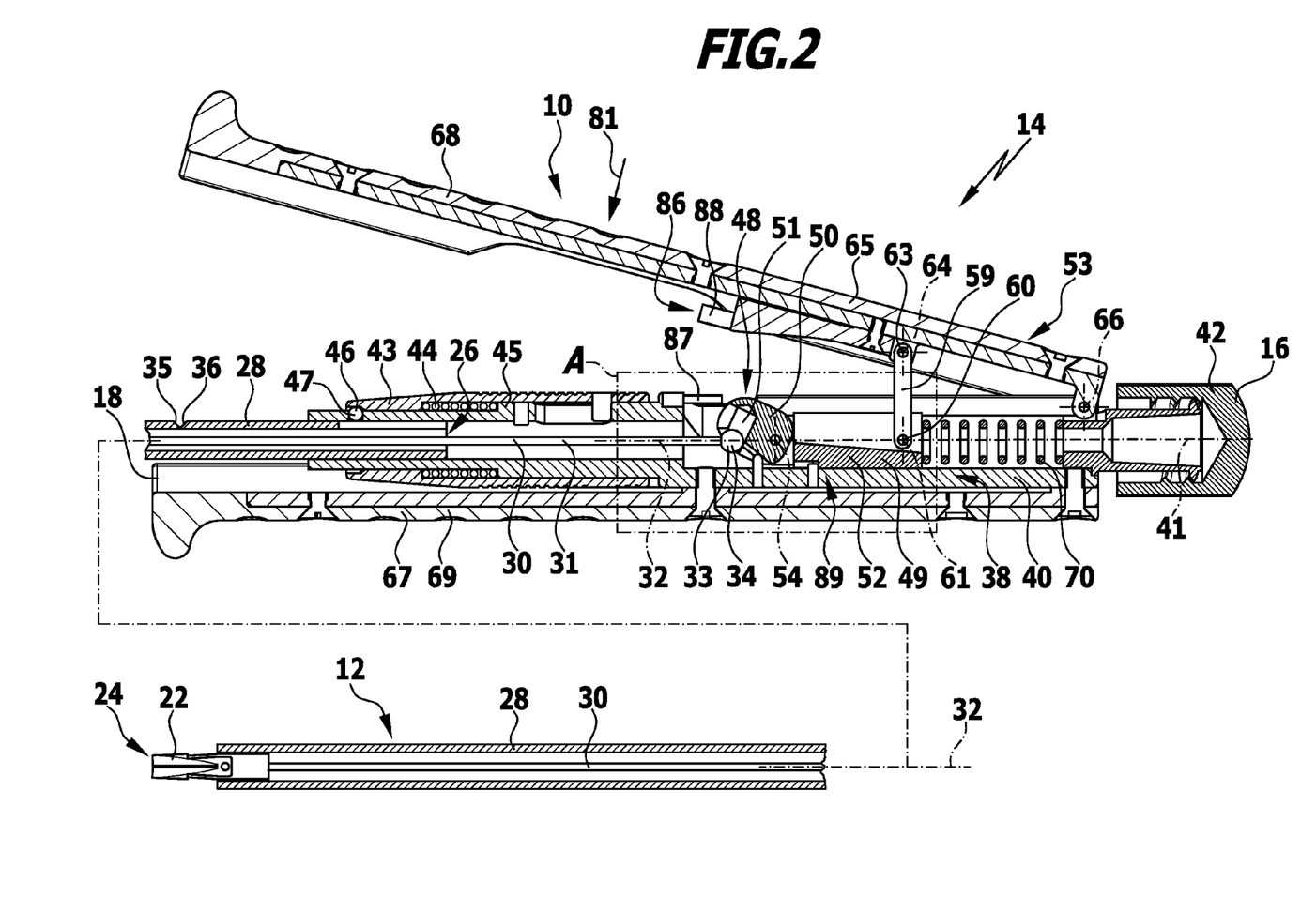
FIG. 2: a longitudinal sectional view of a tubular shaft tool in accordance with the invention comprising the hand grip depicted in FIG. 1 and also a tubular shaft tool connected thereto, wherein a coupling element of the hand grip is in an uncoupling disposition.

The tubular shaft tool 12 has a distal end 22 which simultaneously forms a working end of the tubular shaft instrument 14 and on which there is arranged a surgical clamping element in the form of a two-piece jaw-part 24 for gripping body tissue or a surgical instrument such as a needle. The tubular shaft tool 12 is connectable to the hand grip 10 in releasable manner at a proximal end 26.

In known manner, the tubular shaft tool 12 comprises a tubular shaft 28 and also a force transmission element 30 in the form of a bar 31 which is moveable back and forth therein in the proximal-distal direction and reacts to both tension and pressure, wherein the tubular shaft 28 may be additionally surrounded by an outer sleeve or an outer tube. The tubular shaft 28 and the bar 31 define a tool axis 32 with which they are coaxially aligned. In known manner, an effect can be produced on the jaw-part 24 by a distal end of the bar in order to close and open the jaws so as to grip body tissue or release the surgical instrument such as a needle for instance. This is all well-known so that the illustration relating thereto is only schematic in the region of the distal end 22. The transmission of the force from the bar 31 to the jaw-part 24 is done in such a manner that the jaw-part 24 is closed by a tensional force i.e. when the bar 31 is moved relative to the tubular shaft 28 in the proximal direction.

At the proximal end thereof, the bar 31 has a coupling element 33 in the form of a ball 34 which is arranged outside the tubular shaft 28 at the proximal end thereof.

At a distance from the proximal end 26 thereof, the tubular shaft 28 comprises three connecting elements in the form of recesses which are arranged at an angle of 120° relative to each other taken with respect to the tool axis 32. Of these, only one connecting element 35 in the form of the recess 36 is to be seen in FIG. 2. The connecting elements and also the coupling element 33 serve for coupling the tubular shaft tool 12 to the hand grip 10.

The hand grip 10 comprises a base body in the form of a guiding body 38. The guiding body 38 is in the form of a substantially cylindrical sleeve 40 which defines a grip axis 41 of the hand grip 10. At the proximal end thereof, the sleeve 40 is closed in releasable manner by means of a closure element in the form of a plug 42. The sleeve 40 is open at the distal end so that the tubular shaft 28 and the force transmission element 30 can be introduced for the purposes of coupling to the hand grip 10.

The hand grip 10 and particularly its sleeve 40, and the tubular shaft tool 12 are matched in regard to their dimensions. In connection therewith, the internal diameter of the sleeve 40 is selected in such a way that the tubular shaft 28 can be introduced into the distal end of the sleeve 40 such as to be free from play. The tubular shaft 28 and the bar 31 are thereby aligned coaxially relative to the sleeve 40, and the tool axis 32 can be caused to coincide with the grip axis 41.

A retaining body in the form of an outer sleeve 43 is pushed over the distal end of the sleeve 40, said body being supported on a supporting element of the sleeve 40 in the form of an annular shoulder 45 against the effect of a resilient element in the form of a coil spring 44. The outer sleeve 43 is thereby subjected to a restoring force in the distal direction by the coil spring 44, and it serves in this way to fix connecting elements of the hand grip 10 for the purposes of cooperating with the tubular shaft 28. The connecting elements, of which only one connecting element 46 in the form of a latching ball 47 is shown here, are radially surrounded by the outer sleeve 43 and can be moved through openings in the sleeve 40 into engagement with the three recesses 36 of the tubular shaft 28. The tubular shaft 28 inserted into the sleeve 40 can be fixed thereby to the sleeve 40. For the purposes of connecting and releasing the tubular shaft 28, the outer sleeve 43 can be displaced against the effect of the coil spring 44 in the proximal direction so that the latching balls 47 can be moved more easily into or out of engagement with the recesses 36.

The connecting elements 46 are a component of a coupling device 48 of the hand grip 10 for coupling to the tubular shaft tool 12 which has a further coupling element 49 for coupling to the ball 34 of the bar 31. The coupling element 49 is accommodated in the interior of the sleeve 40 and is aligned coaxially therewith and it can be displaced by the sleeve 40 along the grip axis 41 and in so doing be guided thereby. As is particularly clear from FIG. 3, on the distal side thereof, the coupling element 49 has a receptacle member 50 in which a receptacle 51 for the ball 34 is formed and, at the proximal side thereof, there is a moving member in the form of a displacement member 52 upon which an effect can be produced by means of a gripping device 53 of the hand grip 10. The receptacle member 50 and the displacement member 52 are pivotal relative to each other about a disengaging axis 54 that is oriented transversely with respect to the grip axis 41, wherein the disengaging axis 54 and the grip axis 41 extend along a plane. In connection therewith, the receptacle member 50 and the displacement member 52 inter-engage in the manner of a chain link, for which purpose, there is arranged on the receptacle member 50 at the proximal side thereof, a projection which engages in a slit-like receptacle of the displacement member 52 on the distal side.

Figure 3:
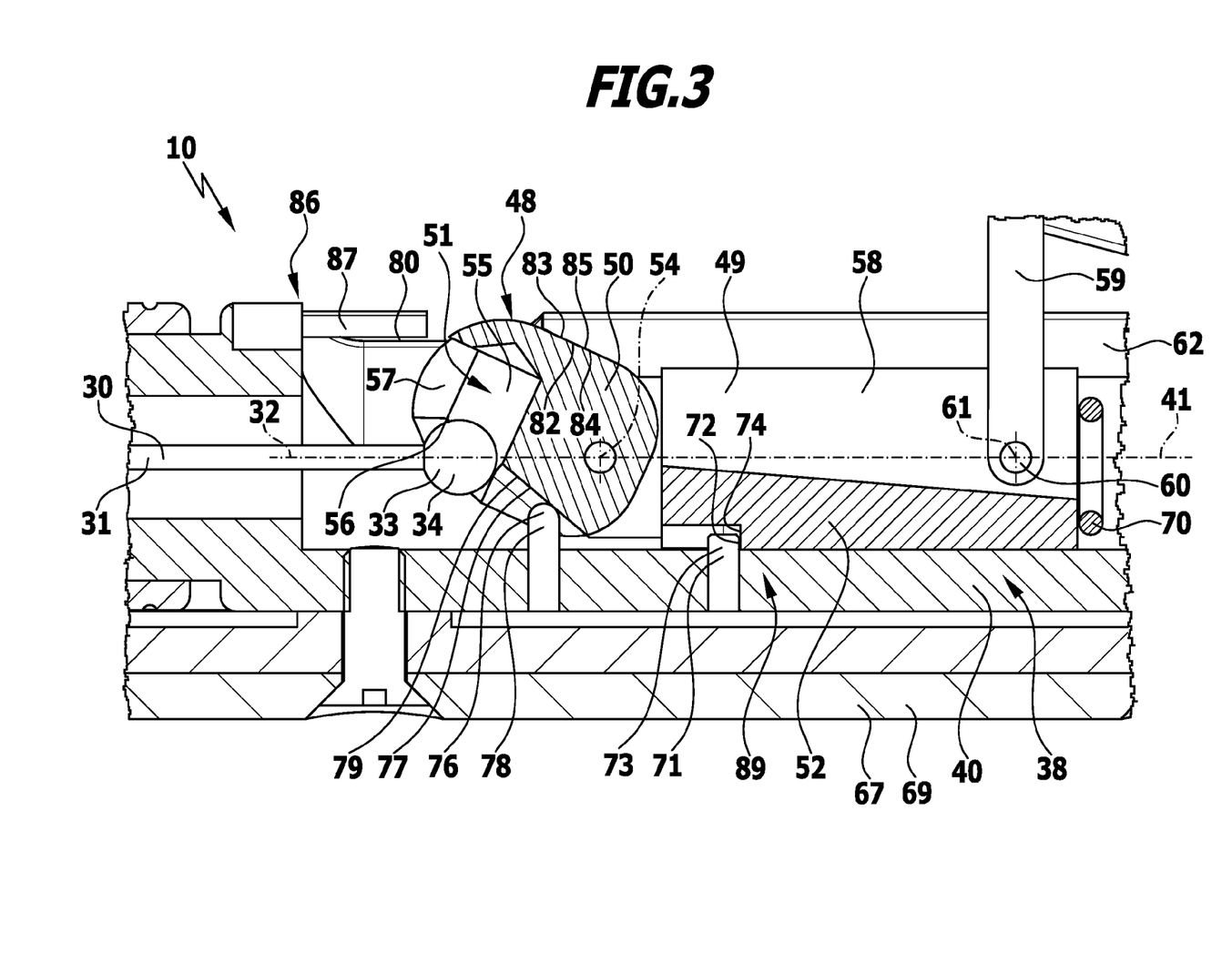
FIG. 3: an enlarged illustration of detail A in FIG. 2.

Adjoining the proximal-side-projection of the receptacle member 50 on the distal side, there is a short cylindrical section thereof, a hemispherical section of the receptacle member 50 being arranged on the distal side thereof. The hemispherical and the cylindrical section are dimensioned with respect to the grip axis 41 in such a way that the receptacle member 50 is accommodated in the sleeve 40 so as to be free from play and can therefore also be guided thereby along the grip axis 41 in displaceable manner.

The receptacle 51 is arranged at the distal end of the receptacle member 50 and it comprises a blind hole 55 which is oriented transversely of the grip axis 41 and has an entry opening 56 for the ball 34. A proximal side wall of the blind hole 55 is axially slit at a through opening 57. If the ball 34 is located in the blind hole 55, the bar 31 can engage through the through opening 57 (FIGS. 4 and 5) so that a force exerted on the coupling element 49 can be transmitted to the bar 31 and thus to the jaw-part 24.

The displacement member 52 has a substantially cylindrical outer contour, and it is dimensioned such that it can be surrounded by the sleeve 40 in play-free manner and can thus be guided thereby along the grip axis 41 in displaceable manner. A longitudinal slot 58 extending in the axial direction is formed in the displacement member 52, the proximal projection of the receptacle member 50 engaging therein on the distal side.

At the proximal side, a linking element 59 which is oriented at an angle to the grip axis 41 engages in the longitudinal slot 58 and provides the operative connection between the gripping device 53 and the coupling element 49. The linking element 59 which is pivotal at an articulated joint 60 about a joint axis 61 is connected to the displacement member 52, wherein the joint axis 61 extends in the plane spanned by the grip axis 41 and the disengaging axis 54.

The linking element 59 projects through a slit-like axial through opening 62 of the sleeve 40. The through opening 62 extends approximately over a third of the length of the sleeve 40, starting approximately from the proximal end thereof. The linking element 59 projects through the through opening 62 such as to be substantially free from play. The linking element 59 is thus guided in the through opening 62 in the course of a relative movement of the sleeve 40 and said element.

The end of the linking element 59 opposite the displacement member 52 is connected in pivotal manner to a first gripping element 65 of the gripping device 53 at an articulated joint 63 where it is pivotal about a joint axis 64 extending in parallel with the joint axis 61. For its part, the first gripping element 65 is pivotally mounted on the sleeve 40 at a pivotal axis 66 which is aligned in parallel with the pivotal axes 61 and 64, wherein the proximal ends of the sleeve 40 and the first gripping element 65 are connected to one another. The distance of the pivotal axis 66 from the articulated joint 63 corresponds approximately to a fifth of the length of the first gripping element 65.

In the course of a pivotal movement of the first gripping element 65 about the pivotal axis 66, the linking element 59 couples the gripping element 65 to the coupling element 49 so that the coupling element 49 is displaced axially relative to the sleeve 40 in dependence on the pivotal angle of the gripping element 65. The linking element 59 thus forms a coupling lever for converting the pivotal movement of the gripping element 65 into a translatory movement of the coupling element 49 which is guided by the sleeve 40.

In addition to the first gripping element 65, the gripping device 53 has a second gripping element 67. The gripping elements 65 and 67 are each shell-like, whereby in particular, they take the form of axially extending, substantially cylindrical half shells 68 and 69 respectively. Starting from the plug 42, the half shells 68 and 69 accommodate therebetween the remaining components of the hand grip 10 and also the proximal end of the tubular shaft tool 12 and they are arranged diametrically opposite each other with reference to the grip axis 41. The gripping elements 65 and 67 extend in the longitudinal direction of the hand grip 10 from the proximal end of the sleeve 40 up to the distal end 18.

In contrast to the first gripping element 65, the second gripping element 67 is firmly connected to the sleeve 40 and is immovable relative thereto. It is also conceivable however that the second gripping element 67 could also be moveable and that it be connected to the sleeve 40 particularly in pivotal manner. For example, the second gripping element 67 could be mounted on the sleeve 40 such as to be pivotal about a pivotal axis that is aligned in parallel with the pivotal axis 66 and transverse to the grip axis 41. It is further conceivable that the second gripping element 67 should project through a through opening of the sleeve 40 that is diametrically opposite the through opening 62 and be operatively connected to the coupling element 49 by a linking element corresponding to the linking element 59.

The pivotal connection of the sleeve 40 and the first gripping element 65 to one another at the respective proximal end makes it possible for the gripping element 65 to be spread out by different amounts relative to the sleeve 40. The maximum spreading angle is governed by the length of the linking element 59 which is connected to the gripping element 65 and to the coupling element 49 held in the sleeve 40.

Starting from a spread disposition, the gripping element 65 can be pivoted about the pivotal axis 66 and thus moved closer to the sleeve 40 thereby displacing the coupling element 49 in the proximal direction and can almost come to abut thereon.

A resilient element in the form of a coil spring 70 is accommodated in the sleeve 40 between the coupling element 49 and the plug 42. The coil spring 70 is supported at the distal end on the coupling element 49 and on the plug 42 at the proximal end thereof, and the coupling element 49 can be displaced in the proximal direction against the effect of the coil spring 70 when the gripping device 53 is actuated.

The coupling of the bar 31 to the coupling element 49 is detailed below and also the use of the hand grip 10 and the tubular shaft tool 12 in the intended manner, wherein it is assumed that the tubular shaft 28 and the bar 31 are pushed as far as possible into the sleeve 40 so that the tool axis 32 and the grip axis 41 are caused to coincide.

For the purpose of coupling to the bar 31, the coupling element 49 is displaced as far as possible in the distal direction. This is effected for example in that a user pivots the first gripping element 65 relative to the sleeve and spreads the distal end thereof as far away as possible from said sleeve. In addition and/or as an alternative thereto, the coil spring 70 subjects the coupling element 49 to a force in the distal direction, which also leads to spreading of the first gripping element 65 away from the sleeve 40. In particular, the coil spring 70 can be designed in such a way that, without a tubular shaft tool 12 being coupled to the hand grip 10, the gripping element 65 will be spread apart to the maximum extent from the sleeve 40 due to the effect of the spring whilst the coupling element 49 adopts a maximally forwardly displaced disposition in the distal direction.

The maximum spreading angle (FIGS. 2 and 3) is given by the length of the linking element 59 on the one hand. Whilst on the other hand, cooperating stop members 71 and 72 are provided respectively on the sleeve 40 and on the displacement member 52, said stop members limiting the displacement path of the coupling element 49 in the distal direction. In the present case, when the stop members 71 and 72 are cooperating, the articulated joints 60 and 63 are oriented in a common plane perpendicularly to the grip axis 41. This ensures that the first gripping element 65 can only be spread away from the sleeve 40 to an extent such that the orientation of the linking element 59 relative to the gripping element 65 and the coupling element 49 is not "overturned", whereby the articulated joint 60 is arranged at most at the same level in the proximal-distal direction as the articulated joint 63.

The stop member 71 is in the form of a stop pin 73 that is oriented transversely relative to the sleeve 40 and held therein, and the stop member 72 is in the form of a shoulder 74 which is formed on the displacement member 52 on the distal side thereof and has a stop surface oriented transversely relative to the grip axis 41.

If as mentioned previously, the first gripping element 65 is spread apart relative to the sleeve 40 and/or if the coupling element 49 is displaced due to the effect of the coil spring 70, then this leads to transferal of the coupling element 49 into a coupling-on disposition. The coupling-on disposition can also be referred to as an uncoupling disposition. This is due to the fact that the hand grip 10 comprises cooperating guidance members 76 and 77 which affect the relative dispositions of the receptacle member 50 and the displacement member 52 when the coupling element 49 is displaced in the distal direction. The guidance member 76 is a guide pin 78 which is oriented transversely relative to the grip axis 41 and is held on the sleeve 40. The guide pin 78 can cooperate with a corresponding guidance surface 79 which is formed on the receptacle member 50 and forms the guidance member 77. Accordingly, if the coupling element 49 is displaced in the distal direction, the guidance surface 79 can slide along on the guide pin 78 before the stop members 71 and 72 couple with one another. Because the guidance surface 79 is oriented such that it is inclined to the grip axis 41, this leads to a pivotal movement of the receptacle member 50 relative to the displacement member 52 about the disengaging axis 54, namely, in such a manner that the receptacle member 50 is pivoted away from the grip axis 41 (FIGS. 2 and 3).

In order to impart to the hand grip 10 as compact a structure as possible, a window-like through opening 80 is formed in the sleeve 40 at the distal side of the axial slit-like through opening 62. The through openings 80 and 62 merge into one another and they are arranged on the same side of the sleeve 40, wherein the through opening 80 extends in the circumferential direction of the grip axis 41 over a larger angle. The receptacle member 50 can engage in the through opening 80 when pivoting about the disengaging axis 54 and can thus be disengaged relative to the grip axis 41, whereby the sleeve 40 can simultaneously be built as compactly as possible.

In the coupling-on disposition, the entry opening 56 of the receptacle 51 is axially free (FIGS. 2 and 3). This enables the ball 34 to be introduced axially into the entry opening 56 and thus into the receptacle 51 and allows the tubular shaft 28 to be connected to the hand grip 10 at the same time. Since the tool axis 32 has already been made to coincide with the grip axis 41, the bar 31 and the coupling element 49 have the correct relative orientation so that the ball 34 can be introduced reliably and correctly into the receptacle 51.

For the purposes of releasing the tubular shaft tool 10 from the tubular shaft instrument 14, the ball 34 can be removed from the receptacle 51 in a corresponding manner, which, as mentioned before, is why the coupling-on disposition of the coupling element 49 is also referred to as an "uncoupling disposition".

Starting from the coupling-on disposition, the coupling element 49 can be transferred into a coupling disposition in which the bar 31 is coupled to the coupling element 49 for the operational employment of the tubular shaft instrument 14.

For the purposes of transferring the coupling element 49 into the coupling disposition, the user can pivot the first gripping element 65 relative to the sleeve 40 thereby decreasing the spreading angle between the gripping element 65 and the sleeve 40. To this end, the gripping element 65 has to be subjected to an actuating force which is directed towards the second gripping element 67 and is symbolized by an arrow 81. Consequently, the coupling element 49 is displaced and guided by the sleeve 40 along the grip axis 41 in the proximal direction due to the coupling provided by the linking element 59. As an alternative or in addition thereto, a user can subject the tubular shaft tool 12, at the jaw-part 24 perhaps and preferably with closed jaw-parts 24, to a force which is directed in the proximal direction and is transmitted to the receptacle member 50 via the ball 34 for the purposes of displacing the coupling element 49.

Guidance members 82 and 83, which are in the form of respective guidance surfaces 84 and 85 that are inclined to the grip axis 41, cooperate during the process of coupling-on to the bar 31. The guidance surface 84 is formed on the sleeve 40 at the proximal side of the window-like through opening 80 at an edge of the slit-like through opening 62. The guidance surface 85 is formed on the receptacle member 50 and, with reference to the grip axis 41, the two guidance surfaces 84 and 85 are located diametrically opposite the guide pin 78 and the guidance surface 79.

During the displacement of the coupling element 49 in the proximal direction, the guidance surfaces 84 and 85 cooperate in such a way that the receptacle member 50 is pivoted relative to the displacement member 42 about the disengaging axis 54, namely, out of the through opening 80 in the direction of the grip axis 41. This leads to the entry opening 56 being pivoted away from the grip axis 41 and becoming axially blocked, whereby the ball 34 is simultaneously pulled, "automatically" so to speak, into the receptacle 51 until the bar 31 projects through the through opening 57 of the receptacle member 50.

Figure 4:
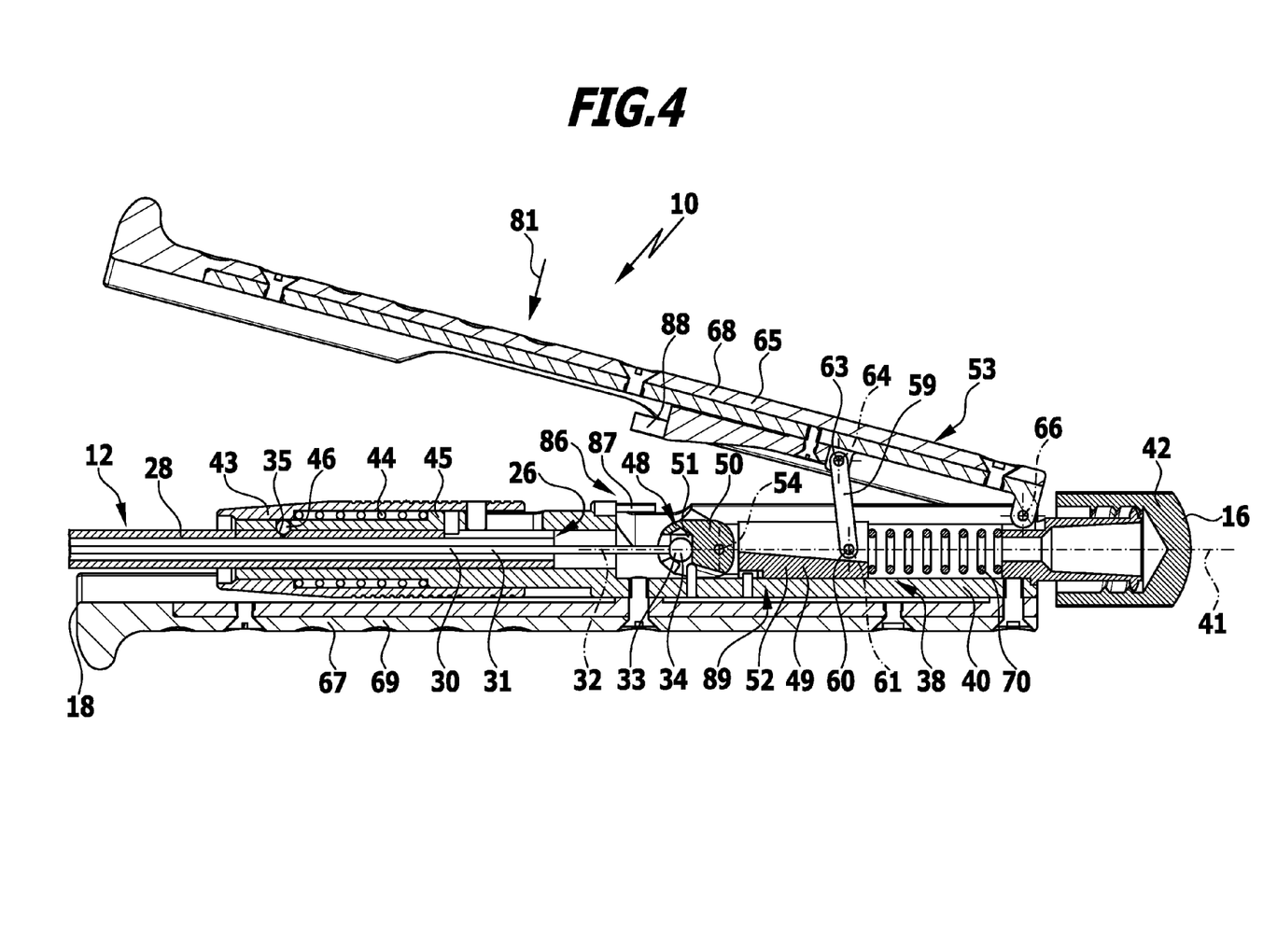
FIG. 4: a longitudinal sectional view of the hand grip depicted in FIG. 1, wherein the coupling element is in a coupling disposition and is located in a non-actuating position

The coupling disposition is adopted when the entry opening 56 is axially blocked and the receptacle member 50 and the displacement member 52 are axially aligned with one another. The coil spring 70 can thereby define the mutually relative position of the coupling element 49 and the sleeve 40 so that the coupling element 49 preferably adopts the uncoupling disposition if the coil spring 70 is arranged to be in a lightly tensioned state between the coupling element 49 and the plug 42 and is under greater tension in the coupling disposition (FIGS. 2 and 4, respectively). As already mentioned, the tubular shaft 28 is likewise fixed to the hand grip 10 in the coupling disposition.

The coupling element 49 which has been transferred into the coupling disposition can adopt a non-actuating position which is associated with a non-actuating disposition of the gripping device 53, and in particular, the gripping element 65. Furthermore, in the non-actuating disposition, the gripping element 65 is still spread apart from the sleeve 40, but at a smaller angle than when the coupling element 49 adopts the uncoupling disposition. The jaw-part 24 is opened in the non-actuating position of the coupling element 49.

For the further use of the hand grip 10 and the tubular shaft instrument 14 in the intended manner, the gripping device 53, and in particular, the gripping element 65 can be transferred from the non-actuating disposition into an actuating disposition and, at the same time, the coupling element 49 from the non-actuating position into an actuating position. To this end, the gripping element 65 can be further subjected to the actuating force 81 in the direction of the second gripping element 67 so that the gripping element 65 is pivoted further relative to the sleeve 40 whilst reducing the spreading angle. The linking element 59 transfers the pivotal movement to the coupling element 49 which is displaced in the proximal direction relative to the sleeve 40 whilst being guided thereby. The displacement is effected against the restoring force of the coil spring 70. The bar 31 coupled to the coupling element 49 is likewise displaced in the proximal direction and the jaw-part 24 is thereby closed. Depending on how far the gripping element 65 is pivoted relative to the sleeve, it can adopt a plurality of actuating dispositions each of which has associated therewith a different actuating position of the coupling element 49 relative to the sleeve 40. The jaw-part 24 is closed or opened to a different extent in the different actuating positions.

Figure 5:
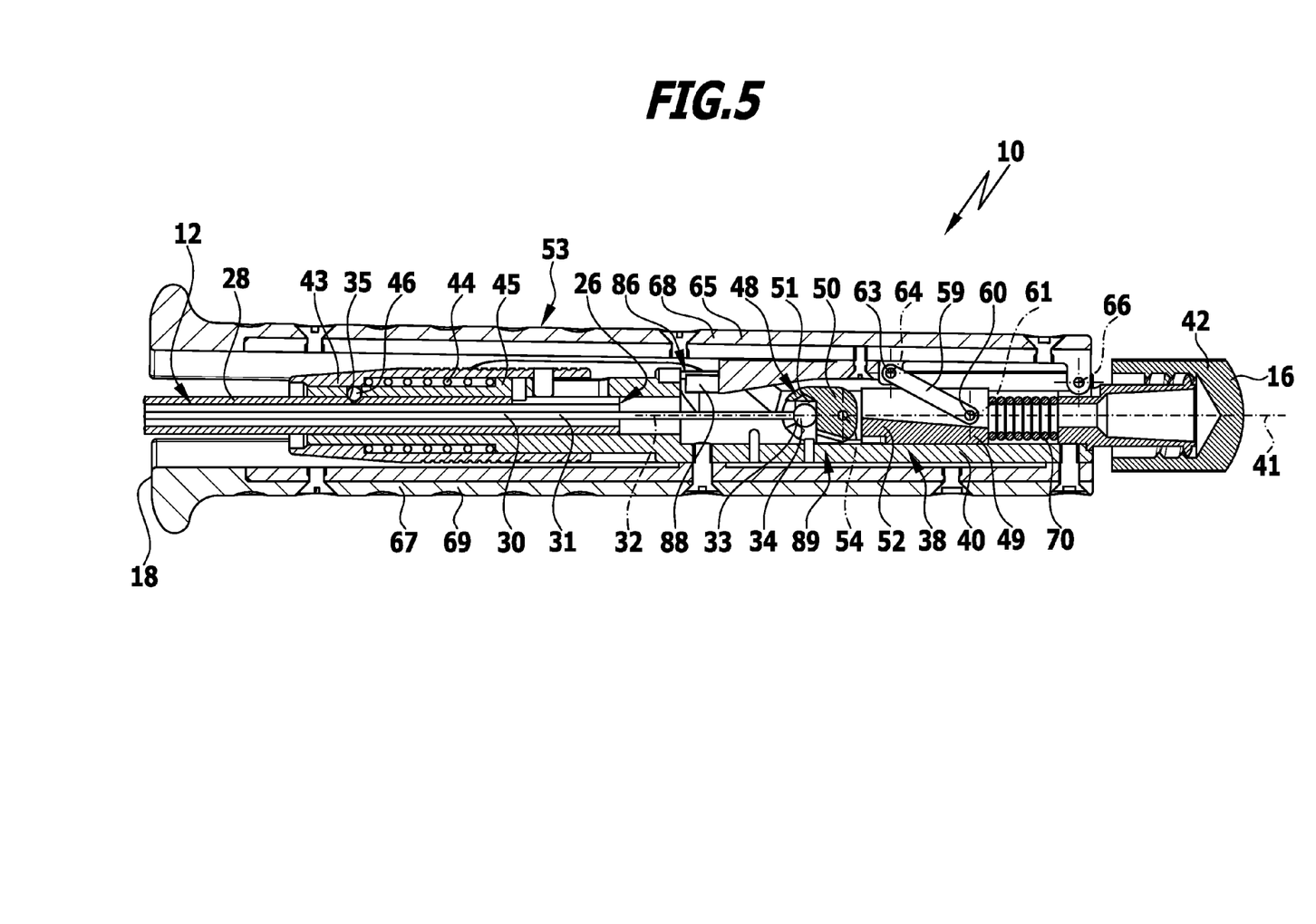
FIG. 5: a longitudinal sectional view of the hand grip depicted in FIG. 1 with the coupling element in the coupling disposition and in an actuating position.

The first gripping element 65 can be pivoted relative to the sleeve 40 to such an extent that it almost abuts against it when extending longitudinally and, together with the second gripping element 67, it forms a substantially cylindrical sleeve which encloses the sleeve 40 (FIG. 5). The gripping element 65 can be fixed in this actuating disposition. For the purposes of fixing the gripping element 65, there is provided a fixing device 86 which is in the form of a latching device. The fixing device 86 comprises cooperating latching members 87 and 88. The latching member 87 is arranged on the sleeve 40 on the distal side of the through opening 80 and projects somewhat into the through opening 80 in the proximal direction. The latching member 88 is fixed to the first gripping element 65 radially inwardly thereof. For the purposes of latching and unlatching, the latching member 88 can be moved in two directions relative to the latching member 87 somewhat transversely relative to the grip axis 41 in order to bring the latching members 87, 88 into engagement and out of engagement. The fixing device 86 can thereby form a so-called rotation barrier.

For the purposes of unlocking the fixing device 86, a user can continue to subject the first gripping element 65 to the actuating force and pivot it towards the sleeve 40 so that the latching members 87, 88 disengage.

In the opposite way, the gripping device 53 can be transferred from the locked actuating disposition into the non-actuating disposition, the coupling element being simultaneously transferred from the actuating position into the non-actuating position. This is effected by the process of pivoting the gripping element 65 relative to the sleeve 40, in particular, utilising the supporting restoring force of the coil spring 70.

In the case of the movements of the coupling element 49 relative to the sleeve 40 that have been described here, it is advantageous for the sleeve 40 to guide the coupling element purely in the axial direction. Consequently, a purely axial movement of the bar 31 can be ensured with the hand grip 10 independently of the actuating disposition of the gripping device 53. This proves to be advantageous because there are no transverse forces oriented transversely of the tool axis 32 and the grip axis 41 effective on the bar 31. The hand grip 10 and the tubular shaft instrument 14 can thus be manipulated in an improved manner. The actuating force that is to be applied to the gripping device 53 by the user can be kept as small as possible due to the missing "dissipation" of the actuating force arising from the occurrence of transverse forces on the bar 31. Moreover, by employing this hand grip 10, one can work in a particularly delicate manner since, in the absence of transverse forces on the bar 31, the actuating force can be adjusted more finely by a user independently of the actuating disposition of the gripping device 53. In addition, in the absence of transverse forces, the wear and tear on the bar 31 can be kept as small as possible. The life span of the tubular shaft tool 12 is thereby increased.

Furthermore, the coupling of the bar 31 to the coupling element 49 or the uncoupling thereof proves to be particularly user-friendly. As previously explained, this is achieved due to the fact that the coupling element 49 can likewise be transferred into the coupling-on or the uncoupling disposition in which the bar 31 can be inserted purely axially into the receptacle or removed therefrom without the occurrence of transverse forces. For user-friendly operation of the hand grip 10 furthermore, the guidance members 76, 77, 82 and 83 and the stop members 71 and 72 have also proved to be advantageous, these members together with the sleeve 40 forming a guiding device 89 of the hand grip 10 for guiding the coupling element 49.

Furthermore, it is expedient for the processes of decoupling and coupling-on the bar 31 that the coupling element 49 be moved along the sleeve 40 in the opposite direction to the transferal from the non-actuating position into the actuating position. As a consequence, this can prevent insofar as possible the bar 31 from being unintentionally decoupled by the coupling element 49 since for this purpose, the gripping element 65 is operated under tension as opposed to being actuated by pressure as is necessary in normal use.

Provision may be made for the tubular shaft instrument 14 to be a surgical mono-polar or bipolar instrument and for an electrical connection element for at least one electrical line to be provided on the hand grip 10 in order to contact the bar 31 and/or the tubular shaft 28 electrically. As an alternative or in addition thereto, an opening may be provided for the passage of a connecting cable to the hand grip 10, via the plug 42 for example, wherein the plug 42 could also be releasable from the sleeve 40 in order to provide access to the proximal end thereof.

The invention claimed is:

1. A surgical hand grip for a surgical tubular shaft instrument, comprising:
   a coupling device for coupling to a tubular shaft tool which has a tubular shaft and a force transmission element that is movable back and forth relative to the tubular shaft,
   the coupling device comprising a coupling element for coupling to the force transmission element and a connecting element for connecting to the tubular shaft,
   a gripping device which is operatively connected to the coupling element and is transferable from a non-actuating disposition into at least one actuating disposition and vice versa thereby changing a mutual relative spacing between the coupling element and the connecting element due to a transferral of the coupling element from a non-actuating position into at least one actuating position,
   a grip axis defined by the hand grip, and
   a guiding device comprising a guiding body for guiding the coupling element along the grip axis during a transfer of the coupling element from the non-actuating position into the at least one actuating position independently of the disposition of the gripping device during the transfer from the non-actuating disposition into the at least one actuating disposition,
   wherein:
   the guiding body comprises an axial sleeve and defines the grip axis,
   the coupling element is mounted in the sleeve in a displaceable manner and is guided by the sleeve during the transfer from the non-actuating position into the at least one actuating position,
   the sleeve comprises an axial slit-like through opening along at least a section of a displacement path which is traversed by the coupling element relative to the sleeve during the transfer from the non-actuating position into the at least one actuating position, and vice versa,
   the sleeve further comprises a window-like through opening which extends over a larger angular range in a circumferential direction of the grip axis than the slit-like through opening, and
   the coupling element, in order to couple the force transmission element thereto or to decouple the force transmission element therefrom is configured to be disengaged relative to the guiding body transversely or at an angle with respect to the grip axis and thereby partially engages in or passes through the window-like through opening.

2. A hand grip in accordance with claim 1, wherein the window-like through opening is arranged on a distal side of the slit-like through opening.

3. A hand grip in accordance with claim 1, wherein the slit-like through opening and the window-like through opening are arranged on a same side of the sleeve in the circumferential direction of the grip axis.

4. A hand grip in accordance with claim 1, wherein the slit-like through opening and the window-like through opening merge into one another.

5. A hand grip in accordance with claim 1, wherein the gripping device comprises a first gripping element which is mounted on the guiding body or on a mounting body that is connected to the guiding body such as to be pivotal about a pivotal axis that is oriented transversely relative to the grip axis.

6. A hand grip in accordance with claim 5, wherein a proximal end of the first gripping element is pivotally mounted on the guiding body or on the mounting body.

7. A hand grip in accordance with claim 5, wherein the first gripping element is fixable in the at least one actuating disposition.

8. A hand grip in accordance with claim 5, wherein the hand grip comprises a linking element which is connected to the first gripping element at a first articulated joint such that it is pivotal about a first joint axis that is oriented transversely relative to the grip axis and is connected to the coupling element at a second articulated joint such that it is pivotal about a second joint axis that is oriented transversely relative to the grip axis.

9. A hand grip in accordance with claim 5, wherein the gripping device comprises a second gripping element which is fixed immovably to the guiding body or to the mounting body.

10. A hand grip in accordance with claim 9, wherein at least one of the first gripping element and the second gripping element is shell-like and surrounds the guiding body in the circumferential direction of the grip axis at least in sections.

11. A hand grip in accordance with claim 1, wherein:
   the coupling element comprises a moving member which is guided by the guiding body in a moveable manner and a receptacle member which is coupled to the moving member and comprises a receptacle for the force transmission element, and the coupling element is transferable from a coupling disposition into an uncoupling disposition and vice versa, wherein an entry opening of the receptacle for the force transmission element is axially blocked in the coupling disposition and the entry opening is axially freed in the uncoupling disposition.

12. A hand grip in accordance with claim 11, wherein the receptacle comprises a blind hole which is formed in the receptacle member incorporating a side wall slit in the axial direction and which is oriented transversely relative to the grip axis.

13. A hand grip in accordance with claim 11, wherein the moving member and the receptacle member are pivotal relative to each other about a disengaging axis which is oriented transversely relative to the grip axis for transferring the coupling element from the coupling disposition into the uncoupling disposition and vice versa.

14. A hand grip in accordance with claim 13, wherein the disengaging axis and the grip axis define a plane.

15. A hand grip in accordance with claim 13, wherein the receptacle member is pivotal away from the grip axis or towards the grip axis for transferring the coupling element from the coupling disposition into the uncoupling disposition and vice versa.

16. A hand grip in accordance with claim 11, wherein the coupling element is moveable along the grip axis for the transferral from the coupling disposition into the uncoupling disposition.

17. A hand grip in accordance with claim 16, wherein the guiding device comprises stop members for limiting a path of movement of the coupling element along the grip axis during the transferral from the coupling disposition into the uncoupling disposition.

18. A hand grip in accordance with claim 11, wherein the guiding device comprises guidance members for guiding the coupling element when being transferred from at least one of the uncoupling disposition into the coupling disposition and from the coupling disposition into the uncoupling disposition.

19. A hand grip in accordance with claim 1, wherein the coupling element is cylindrical or substantially cylindrical at least in sections thereof and is oriented coaxially with the grip axis.

20. A hand grip in accordance with claim 1, wherein the coupling element is slit axially at least in sections thereof.

21. A surgical tubular shaft instrument, comprising:
a hand grip, and
at least one tubular shaft tool which cooperates with the hand grip,
wherein the hand grip comprises:
a coupling device for coupling to the tubular shaft tool which has a tubular shaft and a force transmission element that is movable back and forth relative to the tubular shaft,
the coupling device comprising a coupling element for coupling to the force transmission element and a connecting element for connecting to the tubular shaft,
a gripping device which is operatively connected to the coupling element and is transferable from a non-actuating disposition into at least one actuating disposition and vice versa thereby changing a mutual relative spacing between the coupling element and the connecting element due to a transferral of the coupling element from a non-actuating position into at least one actuating position, a grip axis defined by the hand grip, and a guiding device comprising a guiding body for guiding the coupling element along the grip axis during a transfer of the coupling element from the non-actuating position into the at least one actuating position independently of the disposition of the gripping device during the transfer from the non-actuating disposition into the at least one actuating disposition, wherein:

the guiding body comprises an axial sleeve and defines the grip axis, the coupling element is mounted in the sleeve in a displaceable manner in the sleeve and is guided by the sleeve during the transfer from the non-actuating position into the at least one actuating position, the sleeve comprises an axial slit-like through opening along at least a section of a displacement path which is traversed by the coupling element relative to the sleeve during the transfer from the non-actuating position into the at least one actuating position, and vice versa, the sleeve further comprises a window-like through opening which extends over a larger angular range in a circumferential direction of the grip axis than the slit-like through opening, and the coupling element, in order to couple the force transmission element thereto or to decouple the force transmission element therefrom is configured to be disengaged relative to the guiding body transversely or at an angle with respect to the grip axis and thereby partially engages in or passes through the window-like through opening.

22. A surgical hand grip for a surgical tubular shaft instrument, comprising:
a coupling device for coupling to a tubular shaft tool which has a tubular shaft and a force transmission element that is movable back and forth relative to the tubular shaft,
the coupling device comprising a coupling element for coupling to the force transmission element and a connecting element for connecting to the tubular shaft,
a gripping device which is operatively connected to the coupling element and is transferable from a non-actuating disposition into at least one actuating disposition and vice versa thereby changing a mutual relative spacing between the coupling element and the connecting element due to a transferral of the coupling element from a non-actuating position into at least one actuating position, a grip axis defined by the hand grip, and a guiding device comprising a guiding body for guiding the coupling element along the grip axis during a transfer of the coupling element from the non-actuating position into the at least one actuating position independently of the disposition of the gripping device during the transfer from the non-actuating disposition into the at least one actuating disposition, wherein:

the guiding body comprises an axial sleeve and defines the grip axis, the coupling element is mounted in the sleeve in a displaceable manner and is guided by the sleeve during the transfer from the non-actuating position into the at least one actuating position, the sleeve comprises an axial slit-like through opening along at least a section of a displacement path which is traversed by the coupling element relative to the sleeve during the transfer from the non-actuating position into the at least one actuating position, and vice versa, the sleeve further comprises a window-like through opening which extends over a larger angular range in a circumferential direction of the grip axis than the slit-like through opening, the coupling element comprises a moving member which is guided by the guiding body in a moveable manner and a receptacle member which is coupled to the moving member and comprises a receptacle for the force transmission element, the coupling element is transferable from a coupling disposition into an uncoupling disposition and vice versa, wherein an entry opening of the receptacle for the force transmission element is axially blocked in the coupling disposition and the entry opening is axially freed in the uncoupling disposition, the moving member and the receptacle member are pivotal relative to each other about a disengaging axis which is oriented transversely relative to the grip axis for transferring the coupling element from the coupling disposition into the uncoupling disposition and vice versa, the receptacle member is pivotal away from the grip axis or towards the grip axis for transferring the coupling element from the coupling disposition into the uncoupling disposition and vice versa, and in the coupling disposition, the receptacle member of the coupling element engages in or passes through the window-like through opening.

* * * * *